United States Patent [19]
Podhorez et al.

[11] Patent Number: 6,096,898
[45] Date of Patent: Aug. 1, 2000

[54] ONE POT SYNTHESIS OF 1,2,4-TRIAZOLES

[75] Inventors: David E. Podhorez; John W. Hull, Jr., both of Midland; Christine H. Brady, Rhodes, all of Mich.

[73] Assignee: Dow AgroSciences LLC, Indianapolis, Ind.

[21] Appl. No.: 09/426,797

[22] Filed: Oct. 22, 1999

Related U.S. Application Data

[60] Provisional application No. 60/105,334, Oct. 23, 1998.

[51] Int. Cl.$^7$ ...................... C07D 413/14; C07D 413/04; C07D 409/14; C07D 409/04; C07D 405/14

[52] U.S. Cl. ...................... 548/266.2; 544/124; 544/132; 546/256; 546/268.7; 546/269.7; 546/271.1; 546/271.4; 546/272.4; 548/127; 548/182; 548/183; 548/184; 548/185; 548/186; 548/187; 548/188; 548/189; 548/190; 548/191; 548/192; 548/193; 548/194; 548/195; 548/196; 548/200; 548/201; 548/202; 548/203; 548/204; 548/205; 548/206; 548/213

[58] Field of Search .......................................... 548/266.2

[56] References Cited

U.S. PATENT DOCUMENTS 6,015,826  1/2000  Pechacek et al. ...................... 514/383

*Primary Examiner*—Patricia L. Morris
*Attorney, Agent, or Firm*—Donald R. Stuart

[57] ABSTRACT

One pot synthesis of 1,2,4-triazoles uses thioimidate intermediate and 1,2-dichloroethane solvent.

9 Claims, No Drawings

ONE POT SYNTHESIS OF 1,2,4-TRIAZOLES

RELATED APPLICATION

This application claims priority from U.S. Provisional Patent Application Ser. No. 60/105,334, filed Oct. 23, 1998.

FIELD OF THE INVENTION

This invention provides new synthetic procedures and intermediates for preparing insecticidal 1,2,4-triazoles.

BACKGROUND OF THE INVENTION

A number of 3,5-diphenyl-1H-1,2,4-triazole derivatives have been described in the literature as having acaricidal activity. U.S. Pat. No. 5,482,951; JP 8092224, EP572142, JP 08283261. U.S. patent application Ser. No. 09/048,601, filed Mar. 26, 1998, incorporated herein by reference, discloses a series of highly active new 3-(substituted phenyl)-5-(thienyl or furyl)-1,2,4-triazole compounds that are highly active insecticides.

Although the above mentioned patents and patent applications disclose laboratory methods for preparing the disclosed compounds, a need exists for a commercially applicable route.

SUMMARY OF THE INVENTION

The present invention provides a process for preparing insecticidal compounds of the formula (1)

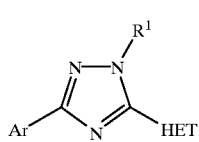

(1)

wherein

Ar is substituted phenyl or pyridyl;

$R^1$ is lower alkyl, haloalkyl, lower alkenyl, lower alkynyl, or alkoxyalkyl;

HET is a group selected from

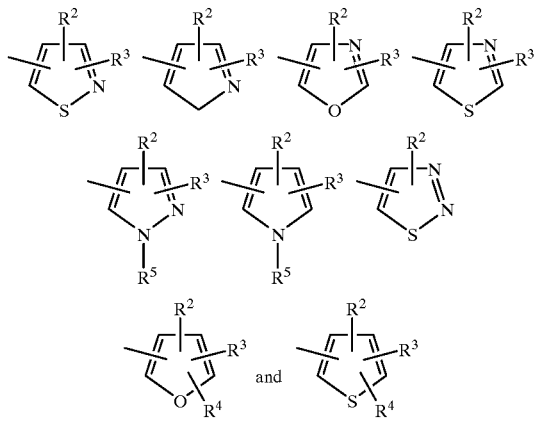

$R^2$ is selected from H, halo, lower alkyl, ($C_7$–$C_{21}$) straight chain alkyl, hydroxy, lower alkoxy, haloalkyl, haloalkoxy, alkoxyalkyl, alkoxyalkoxy, lower alkenyl, haloalkenyl, CN, $NO_2$, $CO_2R^6$, $CON(R^6)_2$, ($C_3$–$C_6$) cycloalkyl, $S(O)_mR^6$, SCN, pyridyl, substituted pyridyl, isoxazolyl, substituted isoxazolyl, naphthyl, substituted naphthyl, phenyl, substituted phenyl, —$(CH_2)_nR^6$, —CH=$CHR^6$, —C≡$CR^6$, —$CH_2OR^6$, —$CH_2SR^6$, —$CH_2NR^6R^6$, —$OCH_2R^6$, —$SCH_2R^6$, —$NR^6CH_2R^6$,

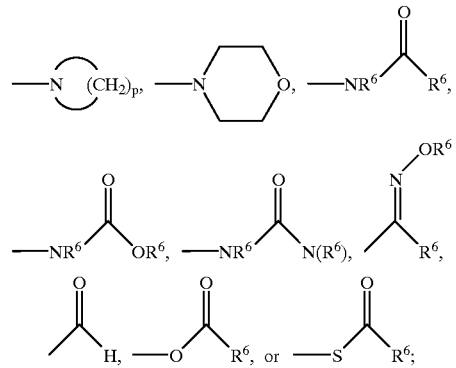

$R^3$ and $R^4$ are independently H, halo, lower alkyl, lower alkoxy, haloalkyl, haloalkoxy, CN, $CO_2R^6$, $CON(R^6)_2$, or $S(O)_m$ alkyl, or if $R^3$ and $R^4$ are attached to adjacent carbon atoms, they may join to form a 5 or 6 member saturated or unsaturated carbocyclic ring which may be substituted by 1 or 2 halo, lower alkyl, lower alkoxy or haloalkyl groups;

if $R^2$ and $R^3$ are attached to adjacent carbon atoms, they may combine to form a 5 or 6 member saturated or unsaturated carbocyclic ring which may be substituted by 1 or 2 halo, lower alkyl, lower alkoxy or haloalkyl groups;

$R^5$ is H, lower alkyl, haloalkyl, lower alkenyl, lower alkynyl, phenyl, or substituted phenyl;

$R^6$ is H, lower alkyl, haloalkyl, lower alkenyl, lower alkynyl, phenyl, or substituted phenyl;

m is 0, 1, or 2; and n is 1 or 2;

p is an integer from 2 to 6;

which comprises the steps of:

(a) reacting a compound of formula (2)

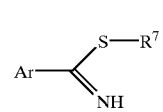

(2)

wherein Ar is as defined in formula (1) and $R^7$ is lower alkyl, or an acid addition salt thereof, with an acid chloride of the formula (3)

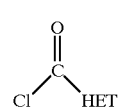

(3)

wherein HET is as defined in formula (1), in 1,2-dichloroethane in the presence of an organic or inorganic base to produce the adduct-intermediate of formula (4)

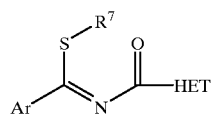

(4)

wherein Ar, $R^7$, and HET are as defined above, (b) without isolating said adduct-intermediate, adding methyl hydrazine to the reaction mixture to produce the compound of formula (1), and (c) adding octane to the reaction mixture to crystallize the product of formula (1).

Preferably an acid addition salt of the reactant of formula (2) is used, and most preferably the acid addition salt is the hydroiodide or the methyl sulfate salt.

In another preferred embodiment, a compound of formula (2)

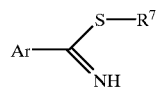

(2)

wherein Ar is substituted phenyl and $R^7$ is lower alkyl, or an acid addition salt thereof, is reacted with an acid chloride of the formula (3a)

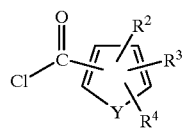

(3a)

wherein Y, $R^2$, $R^3$, and $R^4$ are as defined in formula (1), to produce an adduct-intermediate of formula (4a)

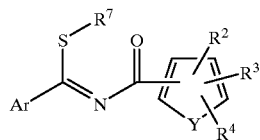

(4a)

wherein Ar, Y, $R^2$, $R^3$, $R^4$ and $R^7$ are as defined above; and the adduct-intermediate of formula (4), is reacted with methyl hydrazine to produce the compound of formula (1a)

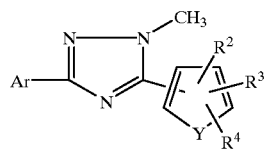

(1a)

wherein Ar is substituted phenyl and $R^2$, $R^3$ and $R^4$ are as defined above.

In a particularly preferred embodiment, a compound of formula (2a)

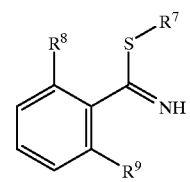

(2a)

wherein $R^8$ and $R^9$ are independently F or Cl, and $R^7$ is lower alkyl, or an acid addition salt thereof, is reacted with an acid chloride of the formula (3b)

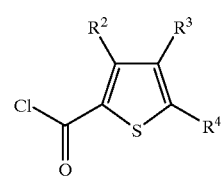

(3b)

wherein $R^2$, $R^3$ and $R^4$ are independently H, $CH_3$, Cl, or Br to produce the adduct-intermediate of formula (4b)

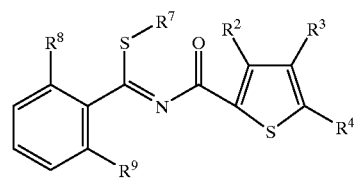

(4b)

wherein $R^2$, $R^3$, $R^4$, $R^7$, $R^8$, and $R^9$ are as defined above, and said adduct-intermediate is reacted with methyl hydrazine to produce the compound of formula (1b)

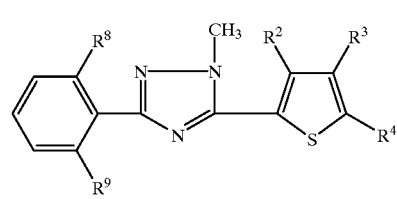

(1b)

wherein $R^2$, $R^3$, $R^4$, $R^8$, and $R^9$ are as defined above. Of particular interest are embodiments wherein $R^7$ is methyl, $R^8$ is F, $R^9$ is Cl, and (a) $R^2$, $R^3$, and $R^4$ are each Cl;

(b) $R^2$ and $R^3$ are each Br and $R^4$ is H; or (c) $R^2$ is $CH_3$, $R^3$ is Cl or Br, and $R^4$ is H.

Most preferred is the embodiment wherein the hydroiodide or methyl sulfate salt of a compound of formula (2b)

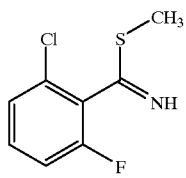 (2b)

is reacted with an acid chloride of the formula (3c)

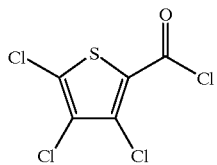 (3c)

to produce the adduct-intermediate of formula (4c)

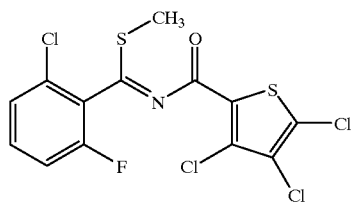 (4c)

and said adduct-intermediate is reacted with methyl hydrazine to produce the compound of formula (1c)

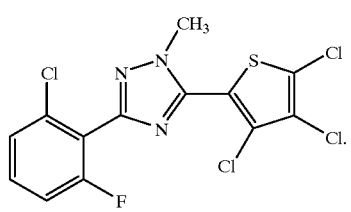 (1c)

DETAILED DESCRIPTION OF THE INVENTION

Throughout this document, all temperatures are given in degrees Celsius, and all percentages are weight percentages unless otherwise stated.

The term "lower alkyl" refers to ($C_1$–$C_6$) straight hydrocarbon chains and ($C_3$–$C_6$) branched and cyclic hydrocarbon groups.

The terms "lower alkenyl" and "lower alkynyl" refer to ($C_2$–$C_6$) straight hydrocarbon chains and ($C_3$–$C_6$) branched hydrocarbon groups containing at least one double or triple bond, respectively.

The term "lower alkoxy" refers to -0-lower alkyl.

The terms "halomethyl" and "haloalkyl" refer to methoxy and lower alkyl groups substituted with one or more halo atoms.

The terms "halomethoxy" and "haloalkoxy" refer to methyl and lower alkoxy groups substituted with one or more halo atoms.

The term "alkoxyalkyl" refers to a lower alkyl group substituted with a lower alkoxy group.

The terms "substituted naphthyl", "substituted thienyl," "substituted pyrimidyl," "substituted pyrazolyl," "substituted pyridyl," and "substituted isoxaxolyl" refer to the ring system substituted with one or more groups independently selected from halo, halo ($C_1$–$C_4$) alkyl, CN, $NO_2$, ($C_1$–$C_4$) alkyl, ($C_3$–$C_4$) branched alkyl, phenyl, ($C_1$–$C_4$) alkoxy, or halo ($C_1$–$C_4$) alkoxy.

The term "substituted phenyl" refers to a phenyl group substituted with one or more groups independently selected from halo, ($C_1$–$C_{10}$) alkyl, branched ($C_3$–$C_6$) alkyl, halo ($C_1$–$C_7$) alkyl, hydroxy ($C_1$–$C_7$) alkyl, ($C_1$–$C_7$) alkoxy, halo ($C_1$–$C_7$) alkoxy, phenoxy, phenyl, $NO_2$, OH, CN, ($C_1$–$C_4$) alkanoyl, benzoyl, ($C_1$–$C_4$) alkanoyloxy, ($C_1$–$C_4$) alkoxycarbonyl, phenoxycarbonyl, or benzoyloxy.

The term "substituted benzenesulfonyl" refers to p-chlorobenzenesulfonyl and p-toluenesulfonyl.

Unless otherwise indicated, when it is stated that a group may be substituted with one or more groups selected from an identified class, it is intended that the groups may be independently selected from the class.

Starting Materials Used in the Process

Alkyl benzthioimidates of formula (2) are known in the literature and are preferably used as their acid addition salt. In this case, tetrafluoroboric acid, hydrogen chloride, hydrogen bromide, hydrogen iodide, or the like, may be used. Thioimidates are readily available through alkylation of the corresponding thioamides which are themselves commercially available or can be made from the amide (*Phosphorus Sulfur* (1985), 25(3), 297–305) or nitrile (*Chem.-Ztg.* (1980), 104(12), 365–7; *J. Chem. Soc.* (1952), 742; *Can J. Chem.* (1985), 63,3075).

Heterocyclic carboxylic acid derivatives used to prepare starting materials of the formula (3) are prepared using conventional methods, as illustrated hereinafter.

Isothiazoles

The isothiazole carboxylic acid intermediates used in the following examples were prepared by the procedure shown in Scheme A. Reaction of an arylacetonitrile, for example benzylcyanide, with sodium hydroxide followed by isoamylnitrite gives the oximino derivative. Reaction of the sodium salt of the oximino derivative with p-toluensulfonyl chloride give the tosylate ester. Reaction of the ester with thioglycoalte esters, in the presence of base yields the alkyl 3-aryl-4-amino-5-isothiazolecarboxylateSee J. R. Beck, R. P. Gajewski and R. E. Hackler, U.S. Pat. Nos. 4,544,752 (1985) and 4,346,094 (1982). The amino group of the isothiazole can the be transformed into a halogen via diazotization chemistry. See J. R. Beck, R. P. Gajewski, *J. Heterocyclic Chem*, 24, 243, 1987. The ester can then be hydrolyzed to the carboxylic acid with sodium hydroxide in dioxane/water.

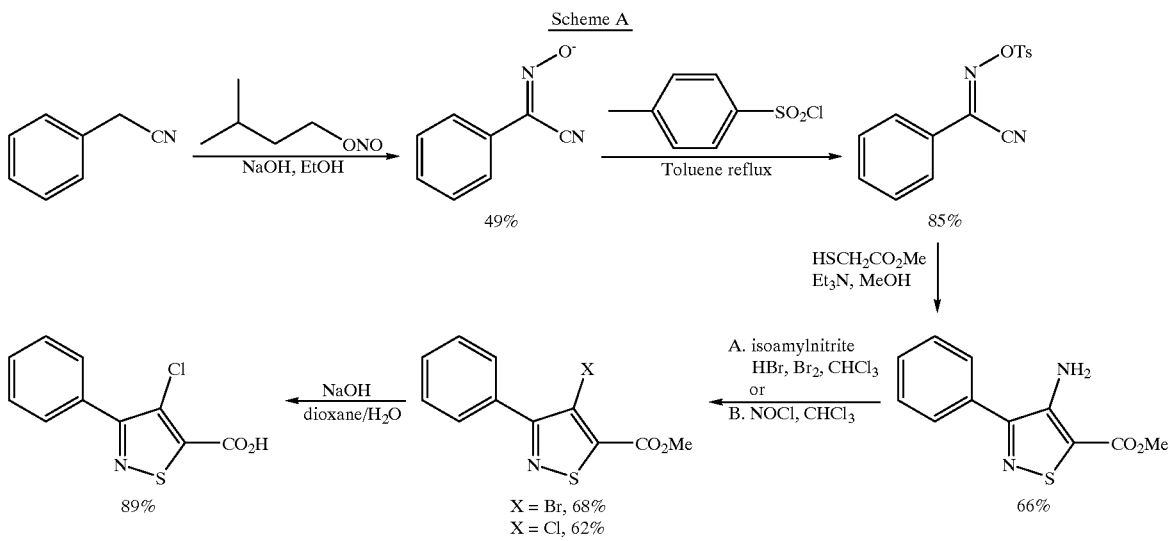

Scheme A

Isoamyl nitrite (32 mL, 0.24 mol) in 30 mL of ethanol was added dropwise to a mechanically stirred solution of benzyl cyanide (23 mL, 0.20 mol) and sodium hydroxide (8.0 g, 0.20 mol) in 100 mL of ethanol, under $N_2$, while cooling in an ice bath. The temperature was maintained at 10–20° C. throughout the addition. Once the addition was complete, the mixture was allowed to warm to room temperature. After stirring at room temperature for two hours, the reaction was diluted with $Et_2O$ (~200 mL) and the resultant precipitate was removed by vacuum filtration, washing with $Et_2O$. The solid was air dried and then vacuum oven dried (70–80° C.) to give 16.45 g (49% yield) of the desired product as a light yellow solid: mp 287–288° C. (decomp.); $^1$H NMR (DMSO) δ 7.58–7.55 (m, 2H), 7.28–7.22 (m, 2H), 7.07–7.02 (m, 1H).

B. α-(p-Toluenesulfonyloxyimino)phenylacetonitrile

A mixture of the oxime salt (, 16.19 g, 96 mmol) and p-toluenesulfonyl chloride (18.30 g, 96 mmol) in 125 mL of toluene was heated to reflux. After refluxing for two hours the reaction was allowed to cool, diluted with EtOAc (200 mL) and washed with $H_2O$ (1×100 mL) and saturated sodium chloride (1×100 mL). The organic phase was dried over anhydrous $MgSO_4$, filtered and concentrated to give 24.37 g (85% yield) of the desired product as light yellow flakes: mp 131–132° C.; $^1$H NMR (CDCl$_3$) δ 7.97–7.94 (m, 2H), 7.82–7.78 (m, 2H), 7.61–7.55 (m, 1H), 7.52–7.39 (m, 4H), 2.47 (s, 3H).

C. Ethyl 3-Phenyl-4-amino-5-isothiazolecarboylxate

Triethylamine (22 mL, 159 mmol) was added dropwise to a mechanically stirred mixture of the tosylate (, 23.92 g, 79.6 mmol) and methyl thioglycolate (8.5 mL, 95.5 mmol) in 200 mL of methanol at such a rate to keep the temperature <45° C. Once the addition was complete, the mixture was allowed to stir at room temperature. After ~2.5 hours the reaction was cooled (precipitate formed upon cooling) and treated with 100 mL of ice/$H_2O$. The resultant solid was removed via vacuum filtration, washing with $H_2O$. The solid was air dried for to give 13.88 g of an orange-yellow solid. Recrystallization from hexane/ethyl acetate and vacuum oven drying (70–80° C.) gave 12.31 g (66% yield) of the desired product as beige needles: mp 115–117° C.; $^1$H NMR (CDCl$_3$) 67 7.73–7.70 (m, 2H), 7.53–7.46 (m, 3H), 5.42 (bs, 2H), 3.91 (s, 3H).

D. Ethyl 3-Phenyl-4-bromo-5-isothiazolecarboylxate

Anhydrous HBr was bubbled into a solution of the aminoisothizole of Example 1C (6.70 g, 28.6 mmol) in 100 mL of CHCl$_3$, while cooling in an ice bath, for 5–10 minutes. The solution was then treated with bromine (5–6 mL) followed by the dropwise addition of isoamylnitrite (5.8 mL, 42.9 mmol). The resultant mixture was allowed to warm to room temperature and then heated to reflux. After refluxing for 15–20 minutes, the reaction was allowed to cool, treated with silica gel and then filtered, washing with $CH_2Cl_2$. The filtrate was concentrated in vacuo to give 9.29 g of a dirty yellow solid. Recrystallization from ethanol and vacuum oven drying (60–70° C.) gave 5.76 g (68% yield) of the desired product as light yellow flakes: mp 120–121° C.; $^1$H NMR (CDCl$_3$) 67 7.81–7.77 (m, 2H), 7.51–7.48 (m, 3H), 3.99 (s, 3H).

E. Ethyl 3-Phenyl-4-chloro-5-isothiazolecarboylxate

Nitrosyl chloride was generated by the dropwise addition of a solution of sodium nitrite (17.25 g, 0.25 mol) in 25 mL of $H_2O$ into 100 mL of concentrated HCl (1.2 mol) in a apparatus similar to that described in *Inorganic Synthesis*, 1953, 4, 48.

The nitrosyl chloride was allowed to bubble into a solution of the aminoisothiazole of Example 1C(5.0 g, 21.3 mmol) in 50 mL of CHCl$_3$, while cooling in an ice bath. Once the formation of nitrosyl chloride was complete the reaction mixture was allowed to warm to room temperature and then heated to reflux. After refluxing for 5 minutes, the reaction was allowed to cool, treated with silica gel and then filtered, washing with $CH_2Cl_2$. The filtrate was concentrated in vacuo to give 5.16 g of an orange solid. Recrystallization from ethanol and vacuum oven drying (60–70° C.) gave 3.37 g (62% yield) of the desired product as light yellow flakes: mp 101–102° C.; $^1$H NMR (CDCl$_3$) 67 7.86–8.83 (m, 2H), 7.51–7.47 (m, 3H), 3.99 (s, 3H).

F. 3-Phenyl-4-chloro-5-isothiazolecarboylic acid A mixture of the ester of Example 2E(3.19 g, 12.6 mmol) in 10 mL of dioxane and 10 mL of 2N NaOH was stirred at room temperature. After stirring for 90 minutes TLC analysis indicated that all of the ester had been consumed. The reaction mixture was diluted with $H_2O$ (20 mL) and washed with $Et_2O$ (2×40 mL). The aqueous phase was acidified with concentrated HCl and extracted with ethyl acetate (3×50 mL). The combined ethyl acetate extracts were washed with saturated sodium chloride (1×50 mL), dried over anhydrous $MgSO_4$, filtered and concentrated in vacuo to give 2.69 g (89% yield) of the desired product as a white solid: mp 196–197° C.; $^1$H NMR (DMSO-$d_6$) 67 14.7–14.3 (bs, 1H), 7.81–7.77 (m, 2H), 7.56–7.54 (m, 3H).

1,2,3-Thiadiazoles

The 1,2,3-thiadiazolecarboxylic acid intermediates used in the following examples can be prepared according to literature procedures (*J.Chem. Soc.*, 1968, 46, 1057).

Thiazole intermediates

Method A

The 2-alky-5-arylthiazole-2-carboxylic acid derivatives were prepared by the route shown in Scheme B. Treatment of the benzoyl acetate with sufluryl chloride gave the intermediate 2-chloro-3-ketoester, which was cyclized with thioacetamide to give the desired thiazole ester derivative. The ester could then be transformed to the carboxylic acid as described above in Example 1F.

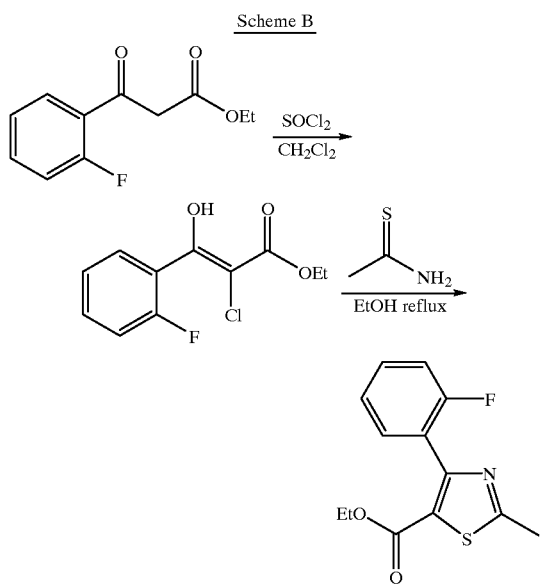

Scheme B

A. Ethyl 2-chloro-2-(2-fluorobenzoyl)acetate

Sulfuryl chloride (4.25 g, 32 mmol) was added dropwise to a solution ethyl 2-(2-flurobenzoyl)acetate (6.30 g, 30 mmol) in CH$_2$Cl$_2$ (75 mL) at room temperature. No exotherm was observed after 30 minutes, only slight bubbling. After stirring overnight TLC analysis indicated that all of the starting material had been consumed. The reaction mixture was treated with H$_2$O (100 mL). The resultant mixture was stirred for 20 minutes and the phases were separated. The organic phase was washed with H$_2$O (2×100 mL), dried over anhydrous MgSO$_4$, filtered and concentrated in vacuo to give 6.85 g (93% yield) of the desired product as an orange oil: $^1$H NMR (CDCl$_3$) 67 8.0–7.9 (m, 1H), 7.6–7.5 (m, 1H), 7.3–7.1 (m, 2H), 5.6 (s, 1H), 4.25 (q, 2H), 1.25 (t, 3H).

B. Ethyl 2-methyl-4-(2-fluorophenyl)-5-thiazole-carboxylate

A mixture of the 2-chloro-3-ketoester (, 3.50 g, 14.3 mmol) and thioacetamide (1.07 g, 14.3 mmol) in absolute ethanol (100 mL) was heated to reflux. After refluxing over the weekend (~3 days), TLC analysis showed one major product and only a trace amount of the starting material present. The reaction mixture was allowed to cool to room temperature, stripped to one half the original volume and then diluted with H$_2$O (200 mL). The solution was made basic with 2N NaOH and the remaining ethanol removed. The aqueous phase was extracted with ethyl acetate (150 mL). The organic phase was washed with H$_2$O (2×100 mL), dried over anhydrous MgSO$_4$, filtered and concentrated onto silica gel. This was chromatographed over silica gel (300 g, MPLC). Eluting with a serial dilution of hexanes to 90% heaxanes/10% ethyl acetate. Isolation of the major product gave 1.95 g (51% yield) of the desired product as a yellow oil: $^1$H NMR (CDCl$_3$) 67 7.6×7.5 (m, 1H), 7.4×7.3 (m, 1H), 7.25×7.05 (m, 2H), 4.2 (q, 2H), 2.7 (s, 3H), 1.2 (t, 3H).

Method B

The second general route to the desired thiazole derivative is shown in Scheme C (*J. Het. Chem.*, 1985, 22, 1621). The cyclization of ethyl 2-chloroacetoacetate with thiourea gave the 2-aminothiazole. The desired 2-halothiazole could then be prepared via diazotization of the aminothiazole. The ester could then be transformed to the carboxylic acid as described above in Example 1F.

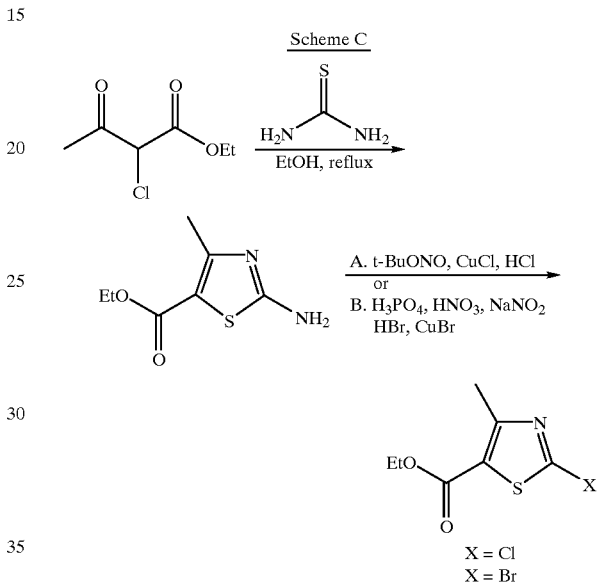

Scheme C

EXAMPLE 3

A. Ethyl 2-Amino-4-methyl-5-thiazolecarboxylate

A mixture of ethyl 2-chloroacetoacetate (50 g, 0.30 mol, Aldrich) and thiourea (45.6 g, 0.60 mol) in 400 mL of absolute ethanol was heated to reflux. After refluxing overnight the reaction mixture was allowed to cool to room temperature and then concentrated to half the original volume in vacuo. The remaining ethanol solution was poured into H$_2$O (1L) and made basic (pH 10) with 2N NaOH. An off-white solid precipitated immediately. The mixture was stirred for ~10 minutes and then the solid was removed by vacuum filtration and dried to give 54.75 g (98% yield) of the desired product as a white solid: $^1$H NMR (CDCl$_3$) 67 5.5 (bs, 2H), 4.25 (q, 2H), 2.5 (s, 3H), 1.35 (t, 3H).

B. Ethyl 2-chloro-4-methyl-5-thiazolecarboxylate

To a mixture of t-butyl nitrite (8.30 g, 80 mmol), cuprous chloride (6.38 g, 65 mmol) in 400 mL of acetonitrile was added Ethyl 2-Amino-4-methyl-5-thiazole-carboxylate (10 g, 54 mmol) in one portion. The thiazole dissolved after 25 minutes, and the reaction was allowed to stir at room temperature for 2 hours. The temperature was then increased to 66° C. for one hour. The solution was gradually allowed to cool to room temperature and filtered. The filtrate was poured into 400 mL of 6N HCl (the solution began fizzing). The solution was stirrred for 20 minutes at which time TLC analysis showed that all of the starting material had been consumed and one product formed. The aqueous mixture was diluted with 700 mL of H$_2$O and then extracted with ethyl acetate (4×400 mL). The ethyl acetate fractions were dried over anhydrous MgSO$_4$, filtered and concentrated in vacuo to give 10.45 g (94% yield) of a reddish oil which crystallized to a reddish-orange solid: $^1$H NMR (CDCl$_3$) 67 4.35 (q, 2H), 2.7 (s, 3H), 1.35 (t, 3H).

C. Ethyl 2-Bromo-4-methyl-5-thiazolecarboxylate

A solution of sodium nitrite (8.56 g, 124 mmol) in 20 mL of H$_2$O was added over a 30 minute period to a mixture of the aminothiazole (7.44 g , 40 mmol), 85% phosphoric acid (50 mL) and 70% nitric acid (25 mL) at –10° C. The mixture began to bubble immediately and an exotherm was observed. A CO$_2$/acetone bath was used to maintain the temperature at –10° C. throughout the addition. An orange precipitate formed and the mixture became very difficult to stir. Once the addition was complete, the mixture was allowed to warm to room temperature and stirred for ~20 minutes. The reaction mixture was then poured into a mixture of hydrobromic acid (20 mL) and cuprous bromide (5.74 g, 40 mmol). After vigorous gas evolution, the mixture was diluted with H$_2$O (650 mL) and filtered to yield a brown solid. The solid was dissolved in ethyl acetate and concentrated onto ~100 g of silica gel and chromatographed over silica gel, eluting with a serial dilution of hexane to 90% hexane/10% ethyl acetate. Isolation of the major product gave 1.92 g (19% yield) of the desired product as a yellow solid: mp 63–65° C.; $^1$H NMR (CDCl$_3$) δ 4.35 (q, 2H), 2.7 (s, 3H), 1.35 (t, 3H).

Pyrrole Intermediates

Two well known routes to generate pyrroles include the Hantzsch synthesis (Rec. Trav. Chem., 1979, 98, 437) and the Knorr synthesis (Die Chemnie Des Pyrroles, Vol. 1, Akademische verlagsgesellschaft, Leipzig, 1934, pp 3–5). The dibromo analog was prepared as described in Example 5.

EXAMPLE 4

4,5-Dibromo-1-methyl-2-pyrrolecarboxylic acid.

A solution of 1-methyl-2-pyrrolecarboxylic acid (0.80 g, 6.4 mmol) and bromine (990 μL, 19.2 mmol) in 10 mL of acetic acid was allowed to stir at room temperature. After three hours the precipitate that had formed was removed by vacuum filtration, washed with H$_2$O and vacuum dried to give 0.94 g (52%yield) of the desired product as a white solid. The intermediate was used without further purification.

Pyrazole Intermediates

The pyrazole intermediates were from commercial sources or readily synthesized according to literature procedures. See, for example, J. Org. Chem., 1966, 31, 1878; J. Soc. Chem. France, 1966, 293. Synthetic routes to pyrazoles have also been reviewed (Advances in Heterocyclic Chemistry, Vol. 6, A. R. Kratritzky and A. J. Boulton, Eds., Academic Press, New York, 1966, pp 347–426; Pyrazole, Pyrazolines, Indazoles and Condensed Rings, R. H. Wiley, Ed., Interscience, New York, 1967, pp 10–64). The pyrazole intermediates can be alkylated using the general procedure described below. This results in a mixture of isomers which can be readily separated via chromatography and the ester converted to the carboxylic acid as described above in Example 1F

EXAMPLE 5

Alkylation of Ethyl 3-methyl-5-pyrazolecarboxylate

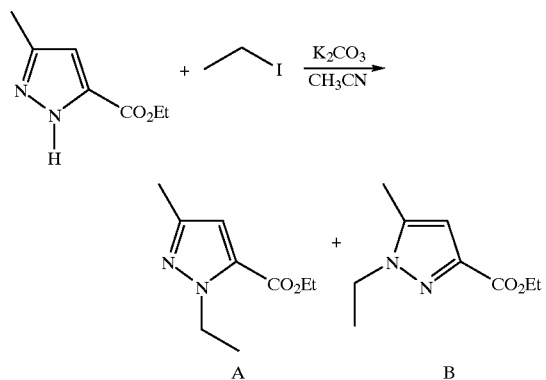

Ethyl iodide (2.0 mL, 25 mmol) was added to a mixture of ethyl 3-methylpyrazole-5-carboxylate (3.85 g, 25 mmol) and potassium carbonate (3.80 g, 27.5 mmol) in 25 mL of acetonitrile and the resultant mixture was heated to reflux. After refluxing over the weekend (~72 h) GC analysis showed <5% starting material remaining. The reaction mixture was poured into H$_2$O (50 mL) and extracted with Et$_2$O (3×50 mL). The combined organic extracts were washed with H$_2$O (1×50 mL), saturated sodium chloride (1×50 mL), dried over anhydrous MgSO$_4$, filtered and concentrated in vacuo to give 4.12 g of a faint yellow oil. This was chromatographed on silica gel (MPLC), eluting with 70% hexane/30% ethyl acetate. The following were isolated:

Ethyl 1-Ethyl-3-methyl-5-pyrazolecarboxylate (A).

g (37% yield), colorless oil: $^1$H NMR (CDCl$_3$) δ 6.60 (s, 1H), 4.53 (q, 2H, J=7.2 Hz), 4.32 (q, 2H, J=7.5 Hz), 2.27 (s, 3H), 1.41 (t, 3H, J=7.4 Hz), 1.37 (t, 3H, J=7.2 Hz).

Ethyl 1-Ethyl-5-methyl-3-pyrazolecarboxylate (B).

1.72 g (38% yield), colorless oil: $^1$H NMR (CDCl$_3$) 67 6.55 (s, 1H), 4.39 (q, 2H, J=6.9 Hz), 4.18 (q, 2H, J=7.2 Hz), 2.30 (s, 3H), 1.43 (t, 3H, J=7.2 Hz), 1.38 (t, 3H, J=7.2 Hz).

Isoxazole Intermediates

The isoxazole intermediates can be prepared according to literature procedures(Chemistry of Heterocyclic Compounds, A Weissberger, Ed., Vol. 17, Wiley-Interscience, New York, 1976, 162). An example of a general route used for the synthesis of isoxazoles intermediates in given in Scheme D.

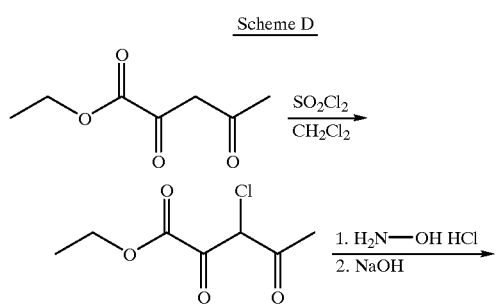

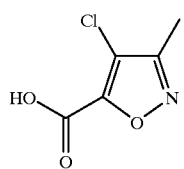

EXAMPLE 6

A. Ethyl 3-chloro-2,4-dioxovalerate

A solution of sulfuryl chloride (7.08 g, 52 mmol) in 15 mL of $CH_2Cl_2$ was added dropwise to a solution of ethyl 2,4-dioxovalerate (7.91 g, 40 mmol) in 125 ml of $CH_2Cl_2$ at room temperature. After three hours TLC analysis indicated that all of the starting material had been consumed. The reaction mixture was washed with $H_2O$ (2×100 mL), dried over anhydrous $MgSO_4$, filtered and concentrated in vacuo to give 7.84 g (81% yield) of the desired product as and orange oil: $^1$H NMR (CDCl$_3$) 67 14.4 (bs, 1H), 5.4 (s, 1H), 4.4–4.3 (m, 4H), 2.5 (s, 3H), 2.4 (s, 3H), 1.4–1.35 (s, 6H) for a 1:1 mixture of tautomers.

B. 3-Methyl-4-chloro-5-isoxazolecarboxylic acid

A solution of ethyl 3-chloro-2,4-dioxovalerate (3.0 g, 15.6 mmol) and hydroxylamine hydrochloride (1.08 g, 15.6 mmol) in a mixuture of 1.5 mL of $H_2O$ and 1 mL of $CH_3OH$ was heated to reflux. After four hours TLC analysis indicated that all of the starting material had been consumed. Sodium hydroxide (0.31 g, 7.8 mmol) was added to the hot solution. After four hours the mixture was allowed to cool to room temperature and concentrated in vacuo. The residue was taken up in a 1:1 mixture to ethyl acetate/$H_2O$. The aqueous layer was made basic with 2N NaOH and separated. The aqueous layer was then acidified with 2M HCl and extracted with ethyl acetate (125 mL). The ethyl acetate extract was washed with $H_2O$ (2×100 mL), dried over anhydrous $MgSO_4$, filtered and concentrated in vacuo to give 600 mg (24% yield) of the desired product a gummy tan solid: $^1$H NMR (CDCl$_3$) 67 8.8 (bs, 1H), 2.3 (s, 3H).

Oxazole Intermediates

The numerous routes to oxazoles have been reviewed (*Chem. Rev.*, 1975, 75, 389).

Carboxylic acid derivatives are converted to the corresponding acid chloride starting material of formula (3) using conventional methods, as illustrated in Example 7:

EXAMPLE 7

3,4,5-Trichloro-2-thiophenecarbonyl chloride

A mixture of 20.4 g (0.088 mole) of 3,4,5-trichloro-2-thiophenecarboxylic acid, 7.3 mL (0.1 mole) of thionyl chloride, 0.2 mL of DMF and 80 mL of 1,2-dichloroethane was heated at reflux temperature for 3 h. The reaction mixture became a clear solution after 1 h of heating. The mixture was allowed to cool to RT, concentrated in vacuo and exposed to high vacuum to give 22.0 g (>98% wt) an oil which solidified upon standing to an off-white powder, mp 37°–41° C.

The Process of the Invention

The following Scheme I illustrates a preferred embodiment of the invention:

Scheme I

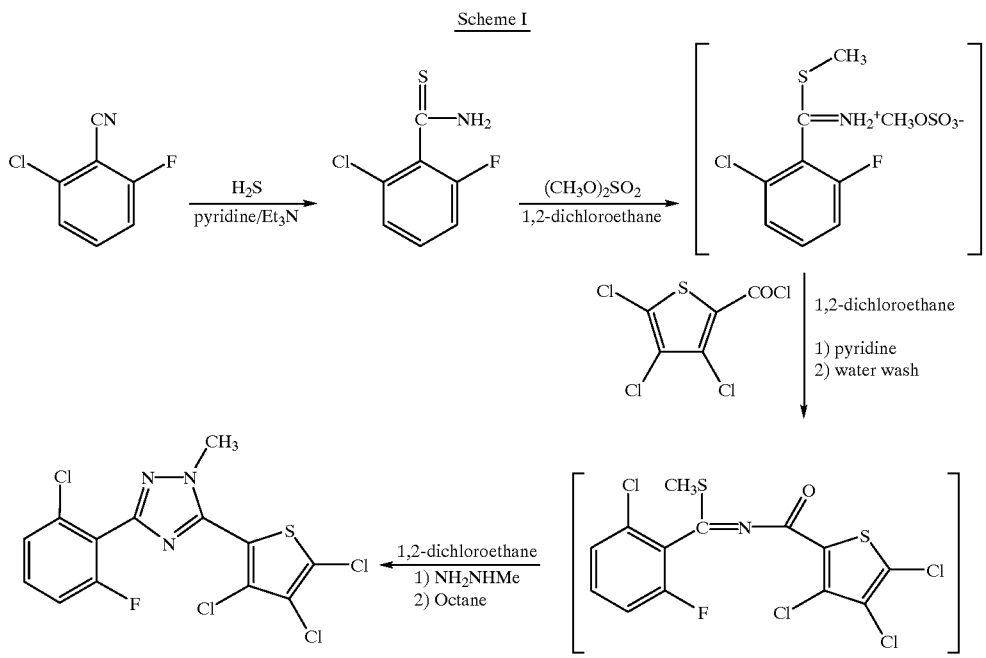

Noteworthy features of the embodiment illustrated in Scheme I include:

1) the methyl sulfate salt of the benzthioimide is used;
2) 1,2-dichloroethane is used as the solvent in each step after preparation of the thioamide starting material;
3) the synthesis is carried out in one pot, without isolation of intermediates;
4) octane is added in the final step to promote crystallization of the product.

The solvent used in the process has a significant effect on the ratio of isomers obtained. The two different isomers arise as a result of the fact that the methyl hydrazine can add in either of two orientations, one resulting in the methyl group being present in the desired position on the nitrogen atom adjacent to the carbon atom bearing the HET group, the other orientation resulting in the methyl being in the undesired position on the nitrogen atom adjacent to carbon bearing the Ar group. Using 1,2-dichloroethane, a 40:1 ratio of the desired isomer has been obtained. When the same conditions were used except that the solvent was toluene, the ratio decreased to 5.5:1. When THF was used, the ratio was only 15:1.

The individual steps in the Scheme I are described in greater detail hereinafter, and particularly in the following Example 1.

The first step in Scheme I is preparation of the thioamide starting material by conversion of 2-chloro-6-fluorobenzonitrile to the thioamide.

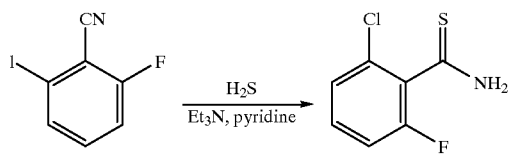

Any of the methods known in the chemical literature can be used for this thioamide formation reaction. Sodium sulfide can be used as the sulfur source, but it has been found most convenient to use hydrogen sulfide gas. Reaction temperatures used are in the −35° to 50° C. range, with −10° to RT most convenient. Any common solvent compatible with the reaction conditions can be used. Pyridine and ethanol are suitable. Any common amine base, for example triethylamine, can be used.

In formation of the thioimidate

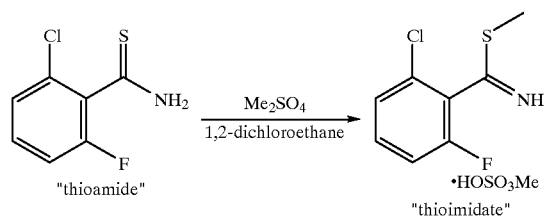

suitable reaction temperatures range from room temperature to the reflux temperature of the solvent. The thioimidate is used directly without isolation in the next transformation.

The thioimidate is next acylated with 3,4,5-trichloro-2-thiophenecarbonyl chloride to give the acylated adduct.

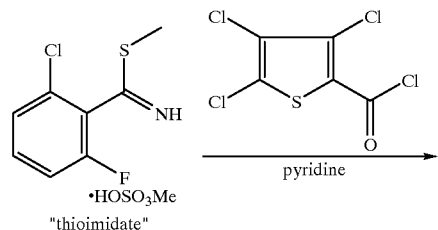

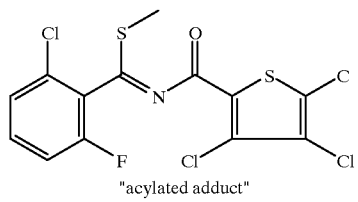

Reaction temperatures in the 0° to 60° C. range are suitable, with temperatures near room temperature most convenient.

The acylated adduct is finally cyclized to the 1,2,4-triazole ring system by treatment with methylhydrazine.

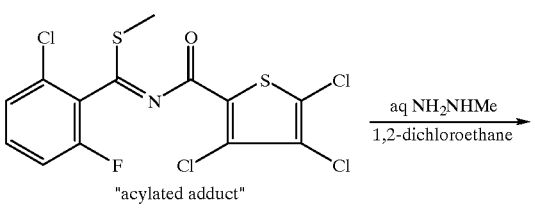

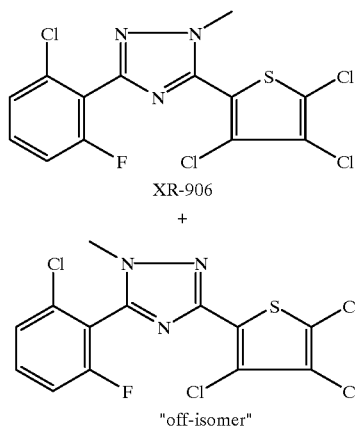

The methylhydrazine can be added neat or as a solution in a compatible solvent such as water. The methylhydrazine can be added all at once to the reaction mixture, or added in portions over a 1 hour time period. The cyclization can be carried out in the temperature range of room temperature to reflux temperature of the solvent. It is most preferred to use a cyclization temperature of 70° C. A 38:1 ratio of 1-methyl-3-(2-chloro-6-fluoro)phenyl-5-(3,4,5-trichloro-2-thienyl)-1H-1,2,4-triazole to its "off isomer" has been obtained under these conditions.

EXAMPLE 8

1-Methyl-3-(2-chloro-6-fluoro)phenyl-5-(3,4,5-trichloro-2-thienyl)-1H-1,2,4-triazole A. Preparation of 2-chloro-6-fluorobenzthioamide in pyridine/triethylamine solvent.

2-Chloro-6-fluorobenzonitrile, (99.1%, 62.2 g, 0.40 mol) was weighed into a 1-L three-necked roundbottom flask equipped with a condenser and an overhead electric stirrer, along with Et$_3$N (78 mL, 56.6 g, 0.56 mol) and 180 mL (176.04 g, 2.23 mol) of pyridine. The reactor was purged with a slow stream of N$_2$ and vented to a 13% bleach solution. The stirring solution was cooled to −19° C. in a CCl$_4$/dry ice bath, and H$_2$S gas (33.6 g, 0.99 mol) was sparged below the liquid surface at a rate of 0.4 g/min over a period of 82 min. During the gas addition, the solution temperature rose to −11° C. The yellow-green solution was allowed to gradually warm to 25° C. and stir overnight with a slow N₂ purge of the reactor head space into bleach solution. The solution was poured into 1.6 L of ice water, stirred, and the resulting white crystals were collected on a buchner funnel and rinsed with additional water. After 2 h of air drying, the moist filter cake was vacuum oven dried for 5 h at 65° C. to give 54.5 g of 2-Chloro-6-Fluorobenzthioamide (72% wt. % yield), mp 155–160° C., having a GC area % purity of 98.8% and containing 1.2% 2-Chloro-6-fluorobenzonitrile.

B. Preparation of 2-chloro-6-fluorobenzthioamide in ethanol/triethylamine solvent.

2-Chloro-6-fluorobenzonitrile, (99.1%, 15.2 g, 0.10 mol) was weighed into a 1-L three-necked roundbottom flask equipped with a condenser and an overhead electric stirrer, along with Et₃N (41 mL, 29.8 g, 0.29 mol) and 54 mL of 95% ethanol. The solution was cooled to 0° C. with an ice bath and H₂S gas (13.5 g, 0.40 mol) was sparged below the liquid surface at a rate of 0.2 g/min over a period of 70 min. The ice bath cooling was continued for 2 h, then the flask was allowed to gradually warm to room temperature. The yellow solution was poured into 426 g of stirring ice water in a 1 L Erlenmeyer flask, and the resulting white solid was collected on a buchner funnel and rinsed with additional water. This filter cake was dissolved in 1,2-dichloroethane and evaporated to dryness on a rotary evaporator (67° C. bath) to ensure dryness, giving 13.42 g (72% weight % yield) of the thioamide as a white solid.

C. 1-Methyl-3-(2-chloro-6-fluorophenyl)-5-(3,4,5-trichloro-2-thienyl)-1H-1,2,4-triazole A mixture of 94.82 g (0.5 mole) of 2-chloro-6-fluorobenzthioamide, 50 mL (0.525 mole) of dimethyl sulfate, and 800 mL of 1,2-dichloroethane was heated at reflux temperature for 1 h. LC analysis indicated complete conversion to the thioimidate. The reaction solution was cooled to RT with ice-bath cooling, and the thioimidate salt precipitated from the solution. To the thick slurry was added 100 mL (1.25 mole) of pyridine. The salts instantly dissolved into solution, followed by immediate precipitation of pyridine salts. After further cooling to 10° C., 125 g (0.5 mole) of 3,4,5-trichloro-2-thiophenecarbonyl chloride dissolved in 200 mL of 1,2-dichloroethane was added in three portions. Temperature of the reaction mixture rose to 20+ C. during each addition and was allowed to cool back to 10° C. before the next addition. The reaction mixture was allowed to stir at RT for 0.5 h. LC analysis indicated major acylated thioimidate and <2% area of starting thioimidate. To the slurry was added 1.0 L of water and the layers separated. LC internal standard analysis of the organics indicated a 94% in-pot yield of the acylated intermediate. The 1,2-dichloroethane solution was heated to 70° C., and a solution of 40 mL (0.75 mole) of methylhydrazine in 60 mL of water was added via a pump over 20 min. The temperature of the reaction mixture was maintained between 70° and 73° C. The solution was heated an additional 2 h, when GC analysis indicate no remaining acylated intermediate and a 38:1 ratio of desired isomer/off-isomer. The reaction mixture was cooled to RT, and 500 mL of octane followed by 1 L of 0.5 N LiOH was added. After stirring for 10 min, the layers were separated. The organic solution was then stirred with 750 mL of a 2% bleach solution for 0.25 h to remove remaining mercaptan compounds. The temperature of the mixture rose to 31° C. during this reaction. The layers were separated and upon concentration of the 1,2-dichloroethane on a rotoevaporator, a tan sandy precipitate formed. This solid was filtered and exposed to vacuum oven drying at 40° C. to give 144.8 g (73% wt) of 1-methyl-3-(2-chloro-6-fluoro)phenyl-5-(3,4,5-trichloro-2-thienyl)-1h-1,2,4-triazole as a tan crystalline powder. GC analysis indicated <0.2% area of the off-isomer, and LC internal standard analysis indicated a 98% purity, giving an overall isolated 72% yield of 1-methyl-3-(2-chloro-6-fluoro)phenyl-5-(3,4,5-trichloro-2-thienyl)-1H-1,2,4-triazole.

We claim:

1. A one pot process for preparing a compound of the formula formula (1)

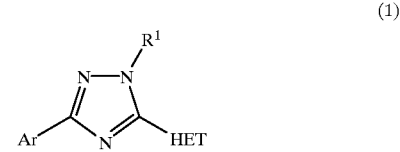

wherein

Ar is substituted phenyl or pyridyl;

$R^1$ is methyl;

HET is a group selected from

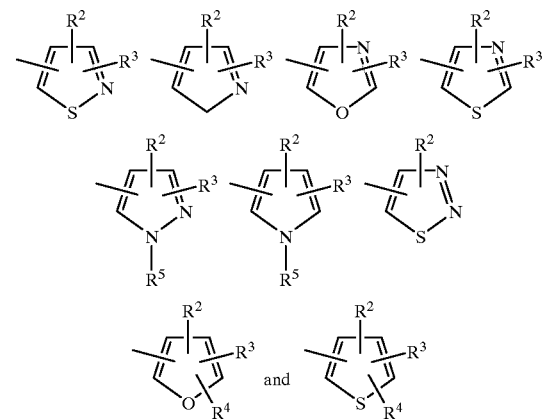

$R^2$ is selected from H, halo, lower alkyl, ($C_7$–$C_{21}$) straight chain alkyl, hydroxy, lower alkoxy, haloalkyl, haloalkoxy, alkoxyalkyl, alkoxyalkoxy, lower alkenyl, haloalkenyl, CN, NO₂, CO₂$R^6$, CON($R^6$)₂, ($C_3$–$C_6$) cycloalkyl, S(O)$_m R^6$, SCN, pyridyl, substituted pyridyl, isoxazolyl, substituted isoxazolyl, naphthyl, substituted naphthyl, phenyl, substituted phenyl, —(CH₂)$_n R^6$, —CH=CHR$^6$, —C≡-CR$^6$, —CH₂OR$^6$, —CH₂SR$^6$, —CH₂NR$^6 R^6$, —OCH₂$R^6$, —SCH₂$R^6$, —NR$^6$CH₂$R^6$,

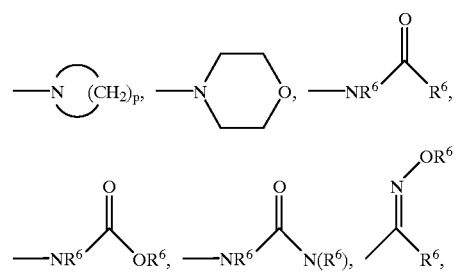

-continued

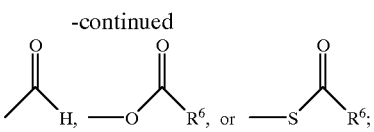

R³ and R⁴ are independently H, halo, lower alkyl, lower alkoxy, haloalkyl, haloalkoxy, CN, $CO_2R^6$, $CON(R^6)_2$, or $S(O)_m$ alkyl, or if R³ and R⁴ are attached to adjacent carbon atoms, they may join to form a 5 or 6 member saturated or unsaturated carbocyclic ring which may be substituted by 1 or 2 halo, lower alkyl, lower alkoxy or haloalkyl groups;

if R² and R³ are attached to adjacent carbon atoms, they may combine to form a 5 or 6 member saturated or unsaturated carbocyclic ring which may be substituted by 1 or 2 halo, lower alkyl, lower alkoxy or haloalkyl groups;

R⁵ is H, lower alkyl, haloalkyl, lower alkenyl, lower alkynyl, phenyl, or substituted phenyl;

R⁶ is H, lower alkyl, haloalkyl, lower alkenyl, lower alkynyl, phenyl, or substituted phenyl;

m is 0, 1, or 2; and n is 1 or 2;

p is an integer from 2 to 6;

which comprises the steps of:

(a) reacting a compound of formula (2)

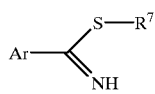

(2)

wherein Ar is as defined in formula (1) and R⁷ is lower alkyl, or an acid addition salt thereof, with an acid chloride of the formula (3)

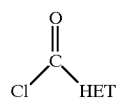

(3)

wherein HET is as defined in formula (1), in 1,2-dichloroethane in the presence of an organic or inorganic base to produce the adduct-intermediate of formula (4)

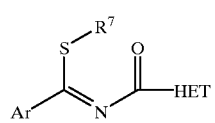

(4)

wherein Ar, R⁷, and HET are as defined above, and (b) without isolating said adduct-intermediate, adding methyl hydrazine to the reaction mixture to produce the compound of formula (1), and (c) adding octane to the reaction mixture to crystallize the product of formula (1).

2. A process of claim 1 wherein an acid addition salt of the compound of formula (2) is used.

3. A process of claim 2 wherein the hydrogen iodide or methyl sulfate salt of the compound of formula (2) is used.

4. A process of claim 1 wherein a compound of formula (2)

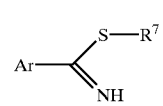

(2)

wherein Ar is substituted phenyl and R⁷ is lower alkyl, or an acid addition salt thereof, is reacted with an acid chloride of the formula (3a)

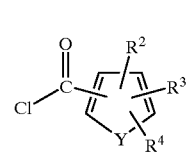

(3a)

wherein Y, R², R³, and R⁴ are as defined in formula (1), to produce an adduct-intermediate of formula (4a)

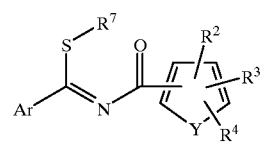

(4a)

wherein Ar, Y, R², R³, R⁴ and R⁷ are as defined above; and the adduct-intermediate of formula (4), is reacted with methyl hydrazine to produce the compound of formula (1a)

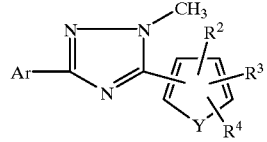

(1a)

wherein Ar is substituted phenyl and R², R³ and R⁴ are as defined above.

5. A process of claim 4 wherein an acid addition salt of the reactant of formula (2) is used.

6. A process of claim 5 wherein the acid addition salt of the reactant of formula (2) is the hydroiodide or the methyl sulfate salt.

7. A process of claim 4 wherein a compound of formula (2a)

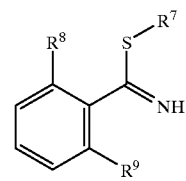

(2a)

wherein R⁸ and R⁹ are independently F or Cl, and R⁷ is lower alkyl, or an acid addition salt thereof, is reacted with an acid chloride of the formula (3b)

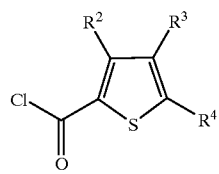

(3b)

wherein R², R³ and R⁴ are independently H, CH₃, Cl, or Br to produce the adduct-intermediate of formula (4b)

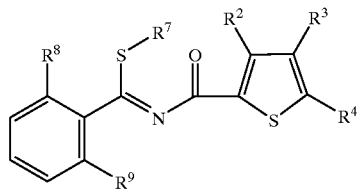

(4b)

wherein R², R³, R⁴, R⁷, R⁸, and R⁹ are as defined above, and, with or without isolation of said adduct-intermediate of formula (4b), said adduct-intermediate is reacted with methyl hydrazine to produce the compound of formula (1b)

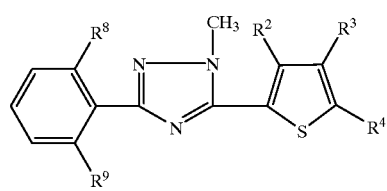

(1b)

wherein R², R³, R⁴, R⁸, and R⁹ are as defined above.

8. A process of claim 7 wherein

R⁷ is methyl, R⁸ is F, R⁹ is Cl, and (a) R², R³, and R⁴ are each Cl;
(b) R² and R³ are each Br and R⁴ is H; or
(c) R² is CH₃, R³ is Cl or Br, and R⁴ is H.

9. A process of claim 7 wherein the hydroiodide or methyl sulfate salt of a compound of formula (2b)

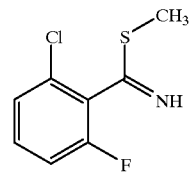

(2b)

is reacted with an acid chloride of the formula (3a)

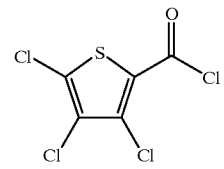

(3c)

to produce the adduct-intermediate of formula (4c)

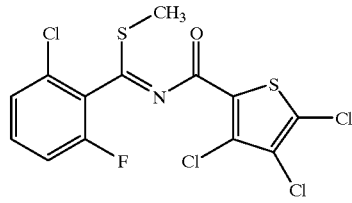

(4c)

and said adduct-intermediate is reacted with methyl hydrazine to produce the compound of formula (1c)

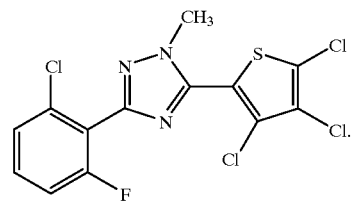

(1c)

* * * * *